(12) United States Patent
Dick et al.

(10) Patent No.: US 9,131,713 B2
(45) Date of Patent: Sep. 15, 2015

(54) PARTICLES OF COLLAGEN MATERIAL AND PROCESS FOR THE PREPARATION

(75) Inventors: Eberhard Dick, Neckargemünd (DE); Simone Walter, Wald-Michelbach (DE)

(73) Assignee: GELITA AG, Eberbach (DE)

( * ) Notice: Subject to any disclaimer, the term of this patent is extended or adjusted under 35 U.S.C. 154(b) by 370 days.

(21) Appl. No.: 13/014,951

(22) Filed: Jan. 27, 2011

(65) Prior Publication Data
US 2011/0135699 A1    Jun. 9, 2011

Related U.S. Application Data

(63) Continuation of application No. PCT/EP2009/059442, filed on Jul. 22, 2009.

(30) Foreign Application Priority Data

Jul. 31, 2008  (DE) .......................... 10 2008 036 576

(51) Int. Cl.
*A23L 1/308*      (2006.01)
*A23L 1/05*       (2006.01)
*B32B 3/00*       (2006.01)
(Continued)

(52) U.S. Cl.
CPC ............ *A23L 1/05625* (2013.01); *A23C 9/137* (2013.01); *A23C 19/082* (2013.01); *A23G 3/346* (2013.01); *A23J 3/04* (2013.01); *A23L 1/24* (2013.01); *A23L 1/305* (2013.01); *A23L 1/307* (2013.01); *A23L 1/3085* (2013.01); *A61K 38/39* (2013.01);
(Continued)

(58) Field of Classification Search
CPC ......... A23L 1/3085; A23L 1/24; A23L 1/305; A23L 1/05625; A23L 1/307; Y10T 428/2982; A23V 2002/00; A23J 3/04; A61K 38/39; A23C 9/137; A23C 19/082; A23G 3/346
See application file for complete search history.

(56) References Cited

U.S. PATENT DOCUMENTS 3,691,281 A * 9/1972 Battista ........................ 514/17.2
3,943,262 A * 3/1976 Winkler et al. ............... 426/250
(Continued)

FOREIGN PATENT DOCUMENTS

DE      000003033885      9/1980
DE      199 34 894        2/2001
(Continued)

OTHER PUBLICATIONS

Segalova et al., Khimiko-Farmatsevticheskii Zhurnal, 15(7): 96-101 (1981).*
(Continued)

*Primary Examiner* — Bethany Barham
*Assistant Examiner* — Lisbeth C Robinson
(74) *Attorney, Agent, or Firm* — Leydig, Voit & Mayer, Ltd

(57) ABSTRACT

In order to provide a product that is suitable as fat substitute in foods, which can be produced simply and inexpensively and is deemed safe from the nutritional physiology viewpoint and with which the typical texture of fat-containing foods can be simulated as favorably as possible, particles of collagen material are proposed which are substantially insoluble and swellable in water, wherein in swollen state the particles have an average diameter of less than approximately 150 μm. A process for the production of this product is additionally proposed.

28 Claims, 2 Drawing Sheets

Figure 1:
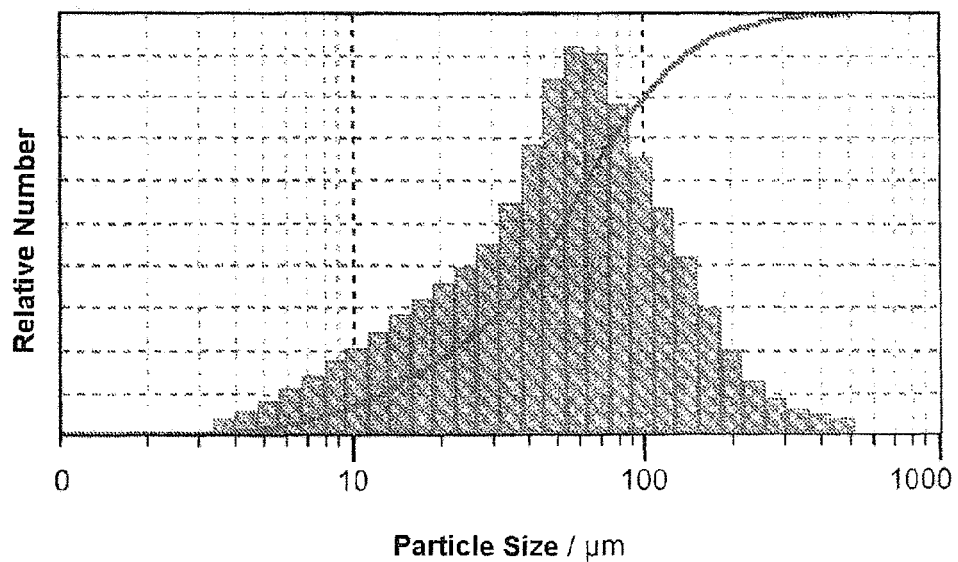

(51) Int. Cl.

| | |
|---|---|
| A61K 9/14 | (2006.01) |
| A61K 8/65 | (2006.01) |
| A23J 1/00 | (2006.01) |
| B02C 19/00 | (2006.01) |
| A23J 3/04 | (2006.01) |
| A23L 1/305 | (2006.01) |
| A23L 1/0562 | (2006.01) |
| A23C 9/137 | (2006.01) |
| A23C 19/082 | (2006.01) |
| A23G 3/34 | (2006.01) |
| A23J 3/00 | (2006.01) |
| A23L 1/24 | (2006.01) |
| A23L 1/307 | (2006.01) |
| A61K 38/39 | (2006.01) |

(52) U.S. Cl.
CPC ........ *A23V 2002/00* (2013.01); *Y10T 428/2982* (2015.01)

(56) References Cited

U.S. PATENT DOCUMENTS

| | | | |
|---|---|---|---|
| 4,615,889 A * | 10/1986 | Fu Lu et al. | 426/140 |
| 5,147,677 A | 9/1992 | Ziegler | |
| 5,284,655 A * | 2/1994 | Bogdansky et al. | 424/422 |
| 5,294,457 A | 3/1994 | Jenkins et al. | |
| 5,877,287 A * | 3/1999 | Lilja et al. | 530/355 |
| 6,037,380 A * | 3/2000 | Venables et al. | 514/781 |
| 6,384,197 B1 | 5/2002 | Weis et al. | |
| 6,716,461 B2 * | 4/2004 | Miwa et al. | 426/34 |
| 2003/0032601 A1 | 2/2003 | Kreuter et al. | |

FOREIGN PATENT DOCUMENTS

| | | |
|---|---|---|
| DE | 100 10 113 | 9/2001 |
| EP | 0 241 896 | 10/1987 |
| EP | 0 945 146 | 9/1999 |
| GB | 2 059 991 | 4/1981 |
| WO | WO 92/10287 | 6/1992 |
| WO | WO 2006/058538 | 6/2006 |
| WO | WO 2006/076051 | 7/2006 |
| WO | WO 2007072064 A2 * | 6/2007 |
| WO | WO 2007104322 A1 * | 9/2007 |

OTHER PUBLICATIONS

Friess et al., Biomaterials, 17: 2289-2294 (1996).*
Google Patent machine translation of DE 19934894A1 downloaded Oct. 29, 2014.*
Kotter, L, *Die Fleischerei*, 47(5):72 (1996).
"Chocolate with Less Fat, More than Evolution, It's Innovation", *Food Marketing & Technology*, 21(1):13-14 (2007).
Danisco: "A new generation of food—tasty and healthy", *Nutraceuticals Now*, pp. 9-11 (2007).
Zunft, H, Ragotzky, K. "Strategien zur Fettsubstitution in Lebensmitteln", in, Fett/Lipid, 99, 1997 No. 6 pp. 204-213.
Schreiber et al., *Gelatin Handbook*, pp. 66-69 and 326, Wiley-VCH Verlag GmbH & Co. KGaA, Weinheim (2007).

* cited by examiner

PARTICLES OF COLLAGEN MATERIAL AND PROCESS FOR THE PREPARATION

The present invention relates to particles of collagen material that are used in particular in the production of foods, as well as a process for their production. The invention additionally relates to compositions comprising such particles.

In the production of low-fat or fat-free foods the problem regularly arises that there is also a deterioration in the taste properties of the product when merely reducing the fat content. The cause of this lies in the at least partial loss of the typical mouth feel of fat-containing foods referred to as texture in this context, wherein this mouth feel that is perceived as creamy and particularly pleasant is caused by a fine emulsion of the fat in the aqueous phase (oil-in-water emulsion).

To simulate this texture at least partially in the case of low-fat or fat-free foods, different substitutes are used that are generally either polysaccharides or proteins (see e.g. J. Michaelides and K. Cooper in: Functional Foods and Nutraceuticals, June 2004). To be able to achieve the desired effect in this case, it is generally important that the substitutes have a sufficiently small particle size that lies in the range of the size of fat droplets in oil-in-water emulsions. Regulating such particle sizes poses difficulties in many cases.

Starch, cellulose, modified cellulose, dextrins, carrageen, xanthan and guar in particular are described as fat substitutes among the polysaccharides. An example of this is the fat substitute described in U.S. Pat. No. 5,294,457, which comprises hydrolysed cereal fibres, carrageen and/or xanthan.

Both plant and animal raw materials are used as proteins. For example, a process for the production of microparticulate protein, in particular based on wheat protein, is described in WO 2006/058538 A1. WO 2006/076051 discloses aqueous protein dispersions starting from soy, milk and egg protein. A water-binding and gelling agent is described in EP 0 241 896 B1 that is produced by drying and grinding defatted pig skin.

The object forming the basis of the present invention is to propose a product suitable as a fat substitute in foods, which can be produced simply and inexpensively and is deemed safe from the nutritional physiology viewpoint, and with which the typical texture of fat-containing foods can be simulated as favourably as possible. A further object is to propose a process for the production of this product.

This object is achieved according to the invention by particles of collagen material, which are substantially insoluble but swellable in water, wherein in swollen state the particles have an average diameter of less than approximately 150 μm.

Collagen is an insoluble fibrous protein of vertebrates and is the main component of connective tissue fibres and bones. In the context of the present invention a collagen material is understood to be a material that is formed to predominant proportions from collagen. In particular, the material can be composed substantially completely from collagen.

An essential property of the particles according to the invention is that they are substantially insoluble in water and are present in the form of a dispersion. However, because of the hydrophilic structure of collagen, the particles have a high swelling capacity and can therefore absorb and bind relatively large quantities of water. As a result, the fat content in foods can be completely or partially replaced by collagen or water, which results in a significant reduction in energy content.

The ability of solid particles to produce a creamy texture similar to fat is also dependent, amongst other factors, on the hardness of the particles in addition to their size. It is important in this case that the particles are small enough and/or soft enough to no longer be sensed in the mouth as particles, which would otherwise result in a grainy or gritty texture.

The inventors have found that the desired effect of a creamy texture can already be achieved with the particles of collagen material according to invention from an average diameter of less than approximately 150 μm in swollen state. The average diameter preferably amounts to approximately 20 μm to approximately 100 μm, further preferred approximately 40 μm to approximately 80 μm. Significantly smaller particle diameters are necessary in some instances according to the prior art when using other starting materials such as e.g. wheat protein.

Because of the high swelling capacity of the particles according to the invention, in dry state the corresponding particle diameters are significantly smaller, generally by approximately 5- to 10-fold. However, the properties of the swollen particles as present in the foods are decisive.

The particles according to the invention are also substantially water-insoluble at elevated temperatures, in contrast to gelatin, which is obtained by extracting collagen-containing materials and which at lower temperatures forms gel structures that gradually dissolve at increasing temperature. A further advantage of the particles according to the invention is therefore that the viscosity or slurry-like consistency of a corresponding dispersion is also retained at higher temperatures because of the insolubility of the collagen material. This high viscosity when hot means that the particles according to the invention can also be used in those foods that are prepared and/or consumed warm or hot.

The particles according to the invention preferably have a polydispersity index of at least approximately 0.3, more preferred of at least approximately 0.5. The polydispersity index is a measure of the distribution of particle size, wherein the index reaches the theoretical maximum value of 1 when all the particles have the same diameter.

In a preferred embodiment of the invention, the collagen material of the particles according to the invention is obtained from bones of vertebrates. The use of collagen from bones has various advantages compared to the use of collage from skin tissue (e.g. cowhide or pig skin). On the one hand, the inventors have found that particles in the desired dimension can be produced more simply from bone collagen than from skin collagen, since fibrous structures are more likely to be obtained in the latter case. This effect is presumably attributable to different cross-linking structures of the collage molecules in bone or in skin tissue.

Moreover, it should be emphasized that particles that are substantially more neutral in taste and smell than corresponding products from cowhide or in particular from pig skin can be produced from bone collagen. Because of their inherent taste, such products are only used in meat or sausage goods, whereas particles from bone collagen that are substantially neutral in taste can also be used in other areas, e.g. for imitation cheese products, dressings or also sweet foods.

While a complex purification of the products is possible to remove taste and odour problems, this is not economically feasible for use in the food sector. The collagen material is preferably obtained from mammals, in particular pigs, cattle, sheep or goats, as well as from poultry or from fish. In the case of collagen material obtained from bone, this preferably comprises ossein. This constitutes a defatted and demineralised bone material that is also used to produce gelatin.

The collagen material preferably has a fat content of less than approximately 5% by weight, in particular less than approximately 2% by weight, respectively in relation to dry mass. The particles according to the invention can therefore also be used for the production of substantially fat-free foods. In particular, correspondingly low fat contents can be obtained without problem by using ossein as collagen material. In this case, the low fat content also contributes to the neutrality in smell and taste of the particles according to the invention, since the odour problem often occurs as a result of an oxidation of the fat during the production process.

A further aspect of the present invention relates to a composition, in particular for the production of foods, comprising the particles according to the invention and a substantially water-soluble material, wherein the particles are dispersed in a matrix of the water-soluble material.

Such a composition has the advantageous effect that dried particles according to the invention can be redispersed very well when they again come into contact with an aqueous medium during production of the food. When drying the particles, which is generally necessary for reasons of storage stability, without the addition of a soluble matrix material aggregates can form, which can only be redispersed with great difficulty. Consequently, the composition according to the invention can be provided both in dried form, wherein the water-soluble material acts as a kind of separating agent, and in a hydrated state, in which the collagen particles are swollen, and the water-soluble material is provided in the form of a true solution, a colloidal solution or a gel.

The water-soluble material can be calorically effective from a nutritional physiology viewpoint, but can also be a soluble dietary fibre. Preferred water-soluble materials are selected from gelatin, collagen hydrolysate, modified starch, dextrins, carob flour, guar, konjac, tara, gum arabic, modified cellulose and mixtures thereof.

Where a good redispersion capacity of the particles according to the invention in cold water is desired, the water-soluble material preferably has a high solubility in cold water.

The proportion of the water-soluble material in the composition preferably amounts to approximately 15 to approximately 75% by weight in relation to dry mass. The proportion required to obtain the desired effect is generally dependent on the type of water-soluble material, wherein this choice is in turn influenced by the respective application or the type of food.

In a further embodiment of the composition according to the invention, this additionally comprises one or more insoluble dietary fibres and/or insoluble proteins besides the collagen particles. The calorie content of the foods can be reduced further by replacing a portion of the collagen particles with calorically ineffective dietary fibres, in addition to the reduction already achieved by partially or completely replacing the fat with the collagen particles or the water bound by the particles.

The dietary fibres and/or proteins are preferably present as particles of the same size range as the particles of collagen material. As a result, these components also contribute to the desired creamy texture of the food by imitating the mouth feel caused by emulsified fat droplets.

Preferred insoluble dietary fibres are selected from materials containing cellulose and/or hemicellulose. Wheat fibres are an example of a suitable dietary fibre.

Insoluble proteins that can be used in the composition according to the invention are preferably selected from zein, casein and/or soy protein. The proteins can be cross-linked, in particular by means of transglutaminase, to make them insoluble.

With respect to the aforementioned process, the object forming the basis of the invention is achieved in that the process for the production of the particles of collagen material according to the invention, comprises the following steps:

a) production of an aqueous slurry of a solid collagen material; and b) mechanical comminution of the collagen material in the slurry, so that particles with an average diameter of less than approximately 150 μm are obtained.

The inventors have found that the comminution of the collagen material in an aqueous slurry constitutes a particularly suitable process to produce particles of collagen material in the size range according to the invention, i.e. particles with an average diameter of less than approximately 150 μm. Preferably, particles with an average diameter of approximately 20 μm to approximately 100 μm, further preferred from approximately 40 μm to approximately 80 μm, are obtained after the mechanical comminution. In the process according to the invention the particles, during comminution, are already present in the swollen state, to which the specified sizes relate.

A theoretical alternative to this process would be the dry grinding of the collagen material. However, in this case the problem arises that the particles stick because of the absorption of small quantities of water from the surrounding area by the dry collagen, and further grinding to the desired size is no longer possible, or that a burnt smell or taste occurs as a result of introducing too high a mechanical energy.

The collagen material used in step a) preferably comprises ossein, which is produced by defatting and demineralising bones. The advantages of using collagen material from bones have already been described in association with the particles according to the invention.

The aqueous slurry is preferably produced by suspending coarsely comminuted collagen material with an average particle size of approximately 2 mm or less in an aqueous medium. This coarse crushing should ensure that the aqueous slurry has an adequate flowability for further processing. Standard processes such as e.g. mincing can be used for the coarse crushing.

The weight ratio of the collagen material to the aqueous medium preferably lies in the range of approximately 1:10 to approximately 1:0.25 during formation of the slurry. An important factor in the choice of this ratio is that the slurry is sufficiently flowable for the subsequent mechanical comminution.

The mechanical comminution of the collagen material in step b) preferably comprises a high-pressure homogenisation. In this process, which is also applied for homogenising the fat content of milk, a reduction of the particle size of the collagen material occurs as a result of shearing, impact and primarily cavitation forces. The pressures applied in this case can lie in the region of approximately 1000 bar, for example.

A further preferred method that can be applied alternatively or additionally during step b) is a wet grinding of the collagen material, e.g. by means of a colloid mill. A procedure that has proved to be particularly advantageous is one in which the collagen material in the slurry is firstly subjected to a wet grinding and then to a high-pressure homogenisation.

It is preferred if the pH value of the slurry is adjusted to a value of approximately 4.5 to approximately 6.5 before or during the implementation of step b) in order to substantially avoid an acid or alkaline hydrolysis of the collagen during the mechanical comminution. Moreover, an oxidising agent can be added to the slurry, if necessary, to obtain a bleaching and/or bactericidal effect.

To produce a composition according to the invention, which besides collagen particles comprises insoluble dietary fibres and/or insoluble proteins, it is advantageous if these are added to the slurry before implementation of step b). These materials are then subjected together with the collagen material to a crushing operation to form particles in the corresponding dimension.

As a result of the process described above, the particles of collagen material according to the invention are obtained as aqueous dispersion, which, depending on the weight ratio of the collagen material to the aqueous medium, has a viscous, creamy to slurry-like consistency and can be used in this form for the production of foods.

To obtain a product with a better storage and transport capacity, the particles obtained in step b) can be dried in an additional step c). The drying of the particles or the composition is preferably achieved by drum drying, spray drying, freeze drying or vacuum belt drying.

The high mechanical stress applied to the collagen material during the comminution in step b) and a thus resulting temperature increase can lead to a hydrolysis of small amounts of collagen in the process according to the invention, i.e. besides the substantially insoluble particles according to the invention water-soluble products such as gelatin or collagen hydrolysate are formed. The extent of the hydrolysis can be limited by the choice of a pH value in the range of approximately 4.5 to approximately 6.5, as described above.

Conversely, as soluble materials the products formed by hydrolysis can also contribute to a better redispersion capacity of the particles according to the invention after the drying operation, as has been explained in detail above. However, since the proportion of soluble materials is generally not sufficient for this purpose, it is preferred according to a further embodiment of the process of the invention that a substantially water-soluble material is added to the slurry after the implementation of step b) and if applicable before the implementation of step c). In this case, a composition can be obtained in which the particles of collagen material are dispersed in a matrix of the water-soluble material, and the subsequent redispersion capacity of the dried particles is significantly improved as a result.

It is also possible to separate gelatin and/or collagen hydrolysate formed by hydrolysis from the collagen particles, should this not be desired in the further processing or use of the particles in foods. In these cases, a different soluble material can be added as matrix instead. However, such a separation is not generally necessary, since the hydrolysis products do not have any disadvantageous effects in the foods to be produced.

The present invention additionally relates to the use of the particles of collagen material described above or the composition described above for the production of foods. In this case, the particles or compositions according to the invention are suitable as fat substitute in many different types of foods, in particular meat and sausage goods, imitation cheese products, instant powder for soups and sauces, dressings, mayonnaise, spreads, yoghurts and creams.

According to a further aspect of the invention, the particles or compositions can also be used for the production of cosmetic or pharmaceutical products. In this case the properties of the collagen particles can be utilised in particular to adjust the desired consistency of ointments or creams. Moreover, dry, sterilised collagen particles, for example, can also be used as wound powder (or as basis for this), wherein the high water-binding capacity also plays an important part.

These and further advantages of the invention are explained in further detail on the basis of the following examples and with reference to the drawing.

Figure 2:
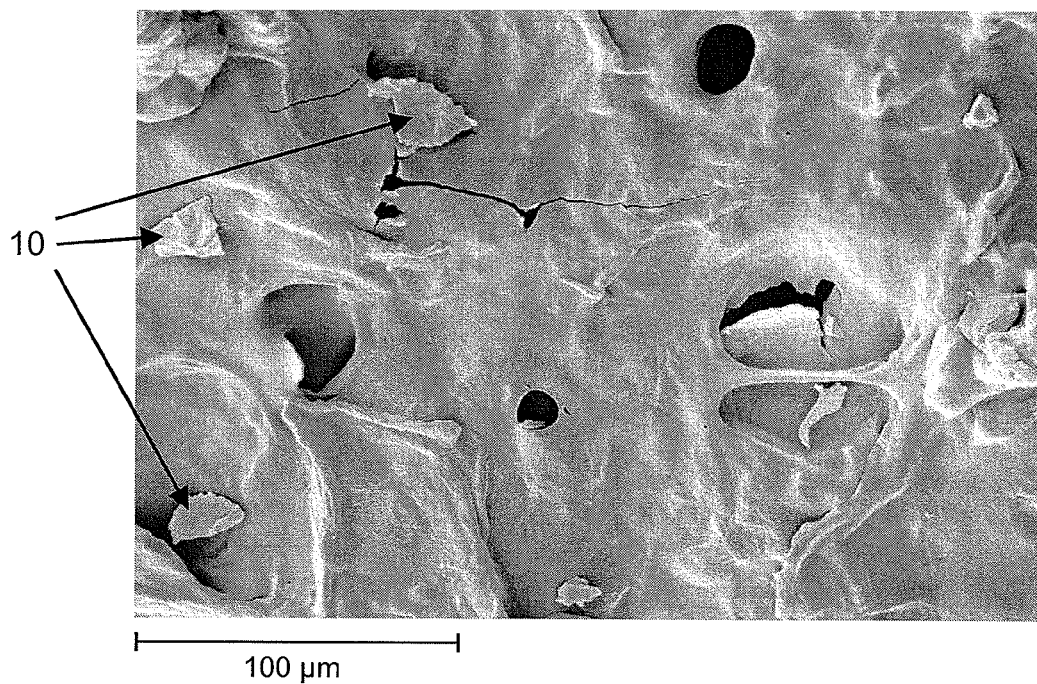

FIG. 1 is an illustration of a typical distribution of size of the particles according to the invention; and FIG. 2 is an electron microscope image of the particles according to the invention.

EXAMPLE 1

Production of Particles According to the Invention from Pig Bones

Ossein from pig bones, i.e. defatted and demineralised bone material, is used as starting material. This was firstly coarsely comminuted with a standard meat mincer, wherein a 5 mm perforated disc was used in a first pass and a 2 mm perforated disc was used in a subsequent second pass.

An aqueous slurry sufficiently flowable to be further processed in a colloid mill was produced from the coarsely comminuted material by adding water in a weight ratio of 1:1. Either a "Comitrol® Processor Model 1500" (manufacturer: Urschel Laboratories Inc.) or a "PUC Colloid Mill Type 60" with recirculating device (manufacturer: Probst & Class GmbH & Co. KG) was used.

The mechanical crushing of the collagen material in the slurry was firstly conducted with a gap width of the colloid mill of 3 mm and then once again with a gap width of 1 mm. After this process step the slurry had a paste-like, but still clearly grainy consistency when rubbed between the fingers.

The pH value of the slurry was adjusted to a value of approximately 5.5 after adding caustic soda solution and approximately 0.5% by weight of hydrogen peroxide was added as bactericide and bleaching agent.

The collagen material was then subjected to a further mechanical comminution by means of a high-pressure homogeniser (model Lab60/15 TBSI, manufacturer: APV/Gaulin). The high-pressure homogenisation was conducted in two consecutive passes at an operating pressure of 1000 bar, a feed and inlet temperature of 50° C. and a throughput of 120 l/h. Whereas after the first pass a very fine-grain structure was still detectable when rubbed between the fingers, the dispersion obtained after the second pass felt structureless and homogeneous.

EXAMPLE 2

Determination of Particle Size and Polydispersity Index

The determination of the average particle size and the polydispersity index as measure of the distribution of size of the collagen particles according to the invention was conducted by means of light scatter. A light-scattering spectrometer S3500 (manufacturer: Particle Metrix) with a measuring range of 0.01 to 2000 μm, two lasers with wavelengths 780 and 405 nm and a nominal laser power of 3 mW were used.

The dispersion of collagen particles obtained according to Example 1 was diluted with water to a dry mass content of approximately 5% by weight and dropped onto the dispersion unit of the measuring device until an adequate particle concentration for the measurement was obtained. The measurement was conducted and evaluated in accordance with the specifications of the equipment manufacturer.

FIG. 1 shows a view of a typical size distribution of the particles according to the invention that was determined with the above-described measurement process. The height of the individual columns (y-axis) in this case corresponds to the relative number of particles in the respective size range (x-axis, logarithmic scale). Typically, for the collagen particles according to the invention produced according to the process described in Example 1 average particle diameters in the range of approximately 40 μm to approximately 80 μm were obtained with a polydispersity index of more than 0.3.

The average particle diameter in the case of the size distribution represented in FIG. 1 amounts to 68.5 μm with a polydispersity index of 0.47.

EXAMPLE 3

Production of a Composition of Collagen Particles and Wheat Fibres

The production occurred as described in Example 1, wherein directly before implementation of the high-pressure homogenisation a quantity of wheat fibres corresponding to the dry mass of collagen material was added to the slurry. At the same time, a corresponding quantity of water was also added, so that the total dry mass content in the slurry remained substantially unchanged.

The two passes of the high-pressure homogenisation were then conducted as described in Example 1, wherein a structureless and homogeneous product when rubbed between the fingers was also obtained here.

The calorie content of the product was halved by replacing half the collagen material with the ineffective wheat fibres.

EXAMPLE 4

Drying the Collagen Particles

The production of dry, storable collagen particles by means of spray drying or drum drying is described below. However, other drying processes can also be additionally used.

Spray Drying

A spray dryer of type Niro P 6.3 with an externally mixing two-fluid nozzle (diameter 2 mm) was used. The dispersion of collagen particles obtained according to Example 1 was heated to approximately 64 to 68° C. and pumped to the two-fluid nozzle of the spray dryer with a flexible tube pump. In a part of the batches 10% by weight of collagen hydrolysate (in relation to the collagen particles) was previously added to the dispersion as soluble matrix material to improve the redispersion capacity of the dried particles.

The process parameters are given in the following Table 1:

TABLE 1

| Parameter | Value |
| --- | --- |
| Drying parameters: | |
| Inlet air temperature | 169-181° C. |
| Outlet air temperature | 105-119° C. |
| Nozzle/atomising air: | |
| Pressure | 1.5 bar |
| Throughput | 23.8 kg/h |
| Drying performance: | |
| Inlet dispersion | 10.6-16.8 l/h |
| Dry substance in the inlet (MA30) | 13.4% |
| Water evaporation | 9.2-14.6 kg/h |

Drum Drying

The dispersion of collagen particles and wheat fibres obtained according to Example 3 was dried on a drum drying plant (R. Simon (Dryers) Ltd., 300 mm diameter and 200 mm width) with a material feed of 12 kg/h, a temperature of 130° C. and a retention time of approximately 25 s.

A mixture of collagen particles and wheat fibres was obtained in the form of thin flakes, which exhibit a good wettability and a very good redispersion capacity in water. The particle size distribution of the redispersible particles is comparable with that prior to drying.

FIG. 2 is an electron microscope image of the drum-dried composition. Individual collagen particles according to the invention are identified with the reference 10.

EXAMPLE 5

Use in Foods

Some examples of application for the diverse use of particles of collagen material according to the invention in foods are specified in this example. Because of the advantageous properties of the particles the fat content in the preparations can be reduced without impairing the sensory quality of the foods.

Either the collagen particles produced according to Example 1 (in the form of the dispersion obtained) or the mixture of collagen particles and wheat fibres produced according to Example 3 (dried) were used for the following recipes, wherein the specified quantities respectively relate to the dry mass. The dry particles can be well redispersed during production of the preparations.

Cheese

A comparison preparation without collagen particles as well as a preparation according to the invention were produced with the composition specified in Table 2 (all details given in percentage by weight):

TABLE 2

| | Comparison Preparation | Preparation according to the Invention |
| --- | --- | --- |
| Collagen particles | — | 10.33% |
| Sodium caseinate | 3.50% | — |
| Kashkaval (Cheddar) | 31.50% | 13.22% |
| Feta cheese | 8.00% | 3.72% |
| Corn starch | 3.50% | 1.49% |
| Fat | 11.00% | 9.92% |
| Emulsifying salts | 1.50% | 1.49% |
| (phosphates) | 0.30% | 0.50% |
| Lactic acid (90%) | 0.70% | 1.49% |
| Common salt | 40.00% | 57.84% |
| Water | | |
| Dry mass | 43.20% | 33.70% |
| Fat in the dry mass | 51.60% | 44.30% |

A first mixture of water, corn starch, lactic acid and common salt was produced as well as a second mixture of the remaining ingredients. The two mixtures were then mixed in a heatable "Stephan Cutter UMC 5 electronic" at 600 rpm and a temperature of 80° C. for approximately 3 minutes.

Compared to the comparison preparation, the cheese according to the invention contains significantly less fat and also a higher water content, which is bound by the collagen particles. Nevertheless, the two preparations have a comparable texture in the sensory assessment.

Mayonnaise and Dressing

A low-fat mayonnaise and a low-fat dressing with collagen particles according to the invention were produced in accordance with the composition specified in Table 3 (all details given in percentage by weight):

TABLE 3

|  | Mayonnaise | Dressing |
| --- | --- | --- |
| Collagen particles | 1.12% | 0.86% |
| Saccharose | 1.75% | 1.35% |
| Instant starch (Pregelflo CH20) | 1.85% | 1.43% |
| Citric acid | 0.25% | 0.19% |
| Common salt | 1.60% | 1.25% |
| Seasoning | — | 9.09% |
| Konjac | 0.45% | 0.21% |
| Water | 80.50% | 76.13% |
| Mustard | 2.70% | 2.09% |
| Vinegar | 0.80% | 0.68% |
| Oil | 8.98% | 6.72% |

A first mixture of water, mustard, vinegar and citric acid was produced as well as a second mixture of the remaining ingredients except for the oil. The two mixtures were then mixed in a heatable "Stephan Cutter UMC 5 electronic" at 600 rpm for approximately 3 minutes (the mayonnaise at a temperature of 60° C. and the dressing at 25° C.). The oil was then added and mixed in for a further minute in the same conditions.

Compared to normal mayonnaise (approximately 80% fat) and commercially available dressings (30-50% fat), the exemplary preparations contain more water and also significantly less fat. The texture and taste is comparable to the conventional products as a result of the use of the collagen particles according to the invention, even in the low proportion of 1.12 or 0.86% by weight.

Compared to the cheese preparation described above, the lower quantity of collagen particles is sufficient in these cases, since the water-binding function is not a primary consideration.

Low-Fat Yoghurt

The influence of collagen particles according to the invention on the texture of low-fat yoghurt was examined.

To produce the yoghurt, 0.75% by weight of collagen particles were dispersed in cow's milk with a fat content of 0.5% and this was heated to 90° C. After cooling to 38° C., the yoghurt culture was added and the mixture was incubated at 38° C. until the target pH value was reached.

A comparison sample was produced in the same way without the addition of collagen particles.

In contrast to the comparison sample, the yoghurt with the collagen particles according to the invention has a smooth, creamy texture. Moreover, it does not exhibit synaeresis, which is attributable to the water-binding properties of the collagen particles.

Chocolate Nut Spread

A reduced-fat chocolate nut spread was produced with the composition specified in Table 4 (all details given in percentage by weight):

TABLE 4

| Collagen particles | 5.16% |
| --- | --- |
| Saccharose | 5.88% |
| Dextrose | 2.58% |
| Fructose | 2.58% |
| Instant starch (Pregelflo CH20) | 1.08% |
| Nutriose | 38.68% |
| Skim milk powder | 5.16% |
| Konjac | 0.77% |
| Water | 24.23% |
| Nut slurry | 6.55% |
| Chocolate | 6.55% |
| Cocoa | 0.65% |
| Flavouring | 0.13% |

A first mixture of water, konjac and instant starch and a second mixture of collagen particles, saccharose, dextrose, fructose, nutriose and skim milk powder were produced. The two mixtures were then mixed in a heatable "Stephan Cutter UMC 5 electronic" at 600 rpm and a temperature of 25° C. for approximately 3 minutes. A mixture of nut slurry, chocolate, cocoa and flavouring was then added and mixed for a further minute in the same conditions.

Compared to commercially available products (approximately 30% fat, 5-10% water and 55-60% carbohydrate), the spread contained more water and also significantly less fat and carbohydrate. The carbohydrate was partially replaced by the sugar substitute nutriose in this case.

The creamy texture and taste are again also comparable with the commercially available product in this example.

The invention claimed is:

1. Particles of collagen material comprising ossein, which are substantially insoluble in water, and which are swellable in water to have a diameter in a swollen state that is approximately 5- to 10-fold larger than the diameter of the particles in a dry state, wherein in the swollen state the particles have an average diameter of 20 to 100 µm, and wherein the particles are produced by high-pressure homogenization or wet-grinding of a solid collagen material comprising ossein in a slurry having a pH value of 4.5 to 6.5.

2. The particles according to claim 1, wherein the particles have a polydispersity index of at least 0.3.

3. The particles according to claim 1, wherein the collagen material is obtained from bones of vertebrates.

4. The particles according to claim 1, wherein the collagen material is obtained from mammals.

5. The particles according to claim 1, wherein the collagen material has a fat content of less than 5% by weight in relation to dry mass.

6. A composition comprising the particles according to claim 1 and a substantially water-soluble material, wherein the particles are dispersed in a matrix of the water-soluble material.

7. The composition according to claim 6, wherein the water-soluble material is selected from gelatin, collagen hydrolysate, modified starch, dextrins, carob flour, guar, konjac, tara, gum arabic, modified cellulose and mixtures thereof.

8. The composition according to claim 6, wherein the proportion of the water-soluble material in the composition amounts to approximately 15 to approximately 75% by weight in relation to dry mass.

9. The composition according to claim 6, wherein the composition additionally comprises one or more insoluble dietary fibers, insoluble proteins, or both.

10. The composition according to claim 9, wherein the dietary fibers, proteins, or both are present as particles of the same size range as the particles of collagen material.

11. The composition according to claim 9, wherein the insoluble dietary fibers are selected from materials containing cellulose, hemicellulose, or both.

12. The composition according to claim 9, wherein the insoluble proteins are selected from zein, casein and soy protein.

13. The composition according to claim 9, wherein the insoluble proteins are cross-linked.

14. A process for the production of the particles of collagen material according to claim 1, comprising:
  a) producing an aqueous slurry of a solid collagen material comprising ossein having a pH value of 4.5 to 6.5; and
  b) mechanically comminuting the collagen material in the slurry to obtain particles with an average diameter of 20 to 100 μm by high-pressure homogenization or wet-grinding.

15. The process according to claim 14, comprising defatting and demineralising bones to produce the solid collagen material.

16. The process according to claim 14, comprising producing the aqueous slurry in a) by suspending coarsely comminuted collagen material with an average particle size of approximately 2 mm or less in an aqueous medium.

17. The process according to claim 16, wherein the weight ratio of the collagen material to the aqueous medium amounts to approximately 1:10 to approximately 1:0.25.

18. The process according to claim 14, wherein mechanically comminuting in b) comprises high-pressure homogenisation.

19. The process according to claim 14, wherein mechanically comminuting in b) comprises wet-grinding.

20. The process according to claim 14, wherein the pH value of the slurry is adjusted to a value of 4.5 to 6.5 before or during the implementation of b).

21. The process according to claim 14, wherein one or more insoluble dietary fibers, insoluble proteins, or both are added to the slurry before implementation of b).

22. The process according to claim 14, further comprising:
  c) drying the particles obtained in b).

23. The process according to claim 22, wherein the drying is conducted by means of drum drying, spray drying, freeze drying or vacuum belt drying.

24. The process according to claim 14, wherein a substantially water-soluble material is added to the slurry after the implementation of b).

25. A food product comprising the particles of collagen material according to claim 1.

26. A cosmetic or pharmaceutical product comprising the particles of collagen material according to claim 1.

27. A food product comprising the composition according to claim 6.

28. A cosmetic or pharmaceutical product comprising the composition according to claim 6.

\* \* \* \* \*